United States Patent
Gammons et al.

(10) Patent No.: US 6,436,341 B1
(45) Date of Patent: Aug. 20, 2002

(54) PACKAGING SYSTEM AND METHOD FOR PACKAGING A STERILIZABLE ITEM TO BE FLASH STERILIZED

(75) Inventors: Clifford E. Gammons, Loudon, TN (US); Richard L. Studer, Villa Hills, KY (US)

(73) Assignee: Adroit Medical Systems, Inc., Loudon, TN (US)

( * ) Notice: Subject to any disclaimer, the term of this patent is extended or adjusted under 35 U.S.C. 154(b) by 0 days.

(21) Appl. No.: 09/761,426

(22) Filed: Jan. 16, 2001

(51) Int. Cl.[7] .......................... H01N 1/00; A61L 11/00; A61L 2/00; A61L 9/00; C23F 11/00
(52) U.S. Cl. .............. 422/1; 422/28; 53/460; 53/491; 206/439
(58) Field of Search .............. 422/1, 28, 460; 53/491; 206/439

(56) References Cited

U.S. PATENT DOCUMENTS

| | | | |
|---|---|---|---|
| 1,306,647 A | * 6/1919 | Wallmuth | 53/491 |
| 2,596,225 A | * 5/1952 | Eaton | 53/491 |
| 3,958,749 A | 5/1976 | Goodrich | |
| 4,358,015 A | 11/1982 | Hirsch | |
| 4,407,442 A | * 10/1983 | Watson et al. | 229/28 R |
| 4,523,679 A | * 6/1985 | Paikoff et al. | 206/370 |
| 4,715,165 A | 12/1987 | Thorogood | |
| 4,813,545 A | * 3/1989 | Chung et al. | 206/621 |
| 5,037,417 A | * 8/1991 | Ternstrom et al. | 609/385.2 |
| 5,163,554 A | 11/1992 | Lampropoulos et al. | |
| 5,224,499 A | * 7/1993 | Zayas | 131/231 |
| 5,356,006 A | * 10/1994 | Alpern et al. | 206/363 |
| 5,447,230 A | * 9/1995 | Gerondale | 206/363 |
| 5,447,699 A | 9/1995 | Papciak et al. | |
| 5,459,978 A | 10/1995 | Weiss et al. | |
| 5,493,845 A | 2/1996 | Adolf et al. | |
| 5,638,661 A | * 6/1997 | Banks | 53/469 |
| 5,671,983 A | 9/1997 | Miller et al. | |
| 5,699,909 A | 12/1997 | Foster | |
| 5,740,943 A | 4/1998 | Shields et al. | |

* cited by examiner

Primary Examiner—Robert J. Warden, Sr.
Assistant Examiner—Imad Soubra
(74) Attorney, Agent, or Firm—Pitts & Brittian, P.C.

(57) ABSTRACT

A package for a sterilizable item is provided. The package includes a tubular member having an open end and a closed end. A reinforcing panel encompassing the closed end is secured to the tubular member proximate the closed end such that the reinforcing panel includes an open end. A cuff portion is attached to the tubular member proximate the open end of the tubular member. The cuff portion includes a first edge secured to the tubular member and a second edge in spaced relation from the first edge, wherein in the cuff portion extends from the open end of the tubular member and substantially overlaps the open end of said reinforcing panel. A portion of the inside surface of the tubular member is thus exposed and defines the width of the cuff portion. In the preferred embodiment, the cuff portion is integral with the tubular member. In this regard, the cuff portion is preferably formed on the tubular member by folding over a circumferential cuff so that a first portion of an outside surface of the tubular member contacts a first portion of the outside surface of the reinforcement panel. A portion of the inside surface of the tubular member is thus exposed and defines the width of the cuff portion. The reinforcement panel provides a buffer layer between an attendant's grasping hand (not shown) and an item placed within the tubular member such that the attendant's hand is not in direct contact with the layer of material of the tubular member that is in contact with the item.

11 Claims, 4 Drawing Sheets

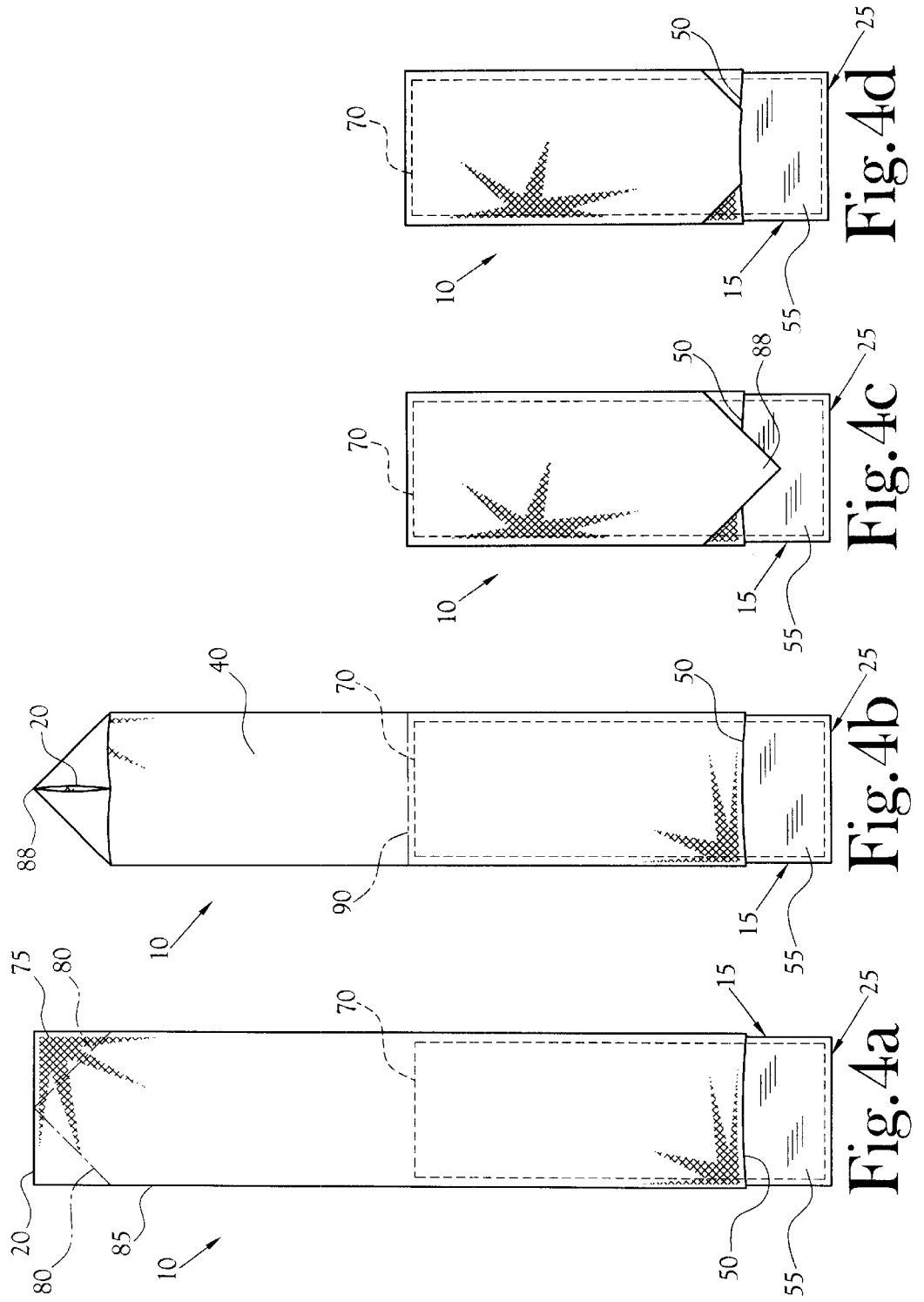

PACKAGING SYSTEM AND METHOD FOR PACKAGING A STERILIZABLE ITEM TO BE FLASH STERILIZED

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of Invention

This invention relates to an improved packaging system, and associated method for packaging a sterilizable item that allows aseptic introduction of a sterile item, particularly one that has been subjected to flash sterilization, into a sterile environment.

2. Description of the Related Art

In both the fields of medical research as well as practical medicine, and particularly the surgical arts, it is well known that maintaining the integrity of a sterile field is of paramount importance. An excellent dissertation of the background of sterile packaging of sterile instruments is set forth in U.S. Pat. No. 5,638,661 which issued to Banks on Jun. 17, 1997. As described by Banks, medical professionals have long recognized the need for maintaining sterile conditions, especially in an operating room. Thus, under standard operating room procedure sterile equipment covers and patient drapes protect and define a sterile surgical field, and all items within the defined surgical field must be sterile.

Such items as equipment covers, patient drapes, and other medical supplies, whether of the single-use variety or reusable, must be sterilized and packaged in a manner that will protect and maintain both the sterility of the item and the sterility of the surgical field during the introduction of the sterile item onto the surgical field. In practice this has meant that many items intended for use in a surgical field are double packaged: a completely sealed outer packaging element surrounds an inner packaging element in or on which the sterilizable item is located. At some point in the production cycle the double-packaged item is sterilized so that when the item arrives at the point of use, both the item and the inner packaging element are sterile.

The inner packaging element is intended to provide a second level of protection and to maintain the sterility of the item and of the sterile field during introduction of the item onto the sterile field. An example of a typical inner packaging element is a sheet of material folded in a so-called central supply wrap (CSR), a name that originally identified a hospital central supply department as the source of the packaged item. The name now designates a particular type of an envelope fold. And, the Banks patent discloses a packaging system for, and a method for, packaging a sterile item in a manner that preserves both the sterility of the sterilized item and the integrity of the sterile field. Other devices typical of art of packaging sterilizable items are those disclosed in the following U.S. Letter Patents:

| U.S. Pat. No. | Inventor Name | Issue Date |
|---|---|---|
| 3,958,749 | Goodrich | May 25, 1976 |
| 4,358,015 | Hirsch | Nov. 9, 1982 |
| 4,715,165 | Thorogood | Dec. 29, 1987 |
| 5,163,554 | Lampropoulos, et al | Nov. 17, 1992 |
| 5,447,699 | Papciak, et al | Sept. 5, 1995 |
| 5,459,978 | Weiss, et al | October 24, 1995 |
| 5,493,845 | Adolf, et al | Feb. 27, 1996 |
| 5,638,661 | Banks | June 17, 1997 |
| 5,671,983 | Miller, et al | Sept. 30, 1997 |
| 5,699,909 | Foster | Dec. 23, 1997 |
| 5,740,943 | Shields, et al | April 21, 1998 |

Banks discloses a packaging system for a sterilizable item that includes an inner packaging element defined by a sterilizable flexible tubular member having a closed end and an open end. According to Banks, the sterilizable item is placed into the tubular member so that the item contacts a portion of an inside surface at the closed end of the tubular member. A border portion is formed on the tubular member so that a first edge of the border portion is attached to the tubular member proximate the opening of the tubular member for the circumference of the opening and a second opposing edge is spaced apart from the first edge by the width of the border portion. The border portion is preferably formed on the tubular member by folding over a circumferential cuff so that a first portion of an outside surface of the tubular member contacts a second portion of the outside surface. In use, a non-scrubbed attendant holds the closed end of the tubular member. With a second hand, the attendant grasps the edge of the border portion at the side of the item. The attendant pulls on the edge of the border portion, at alternate sides of the item, until the tubular member has been inverted to expose generally the entire inside surface of the tubular member, while in the process covering the attendant's hand and forearm with the inverted tubular member. With hand and forearm thus covered and protected, the non-scrubbed attendant may aseptically place the item directly onto the sterile surgical field, eliminating the need for a scrubbed assistant. However, because the tubular member is only a single ply, there is an inherent risk of compromising the sterility of the item, and the sterile field. In this regard, if there is any slight tear or rip in the portion of the tubular member encompassing the sterilized item, and the attendant's hand touches the sterile item, the item has been contaminated. Of course, if the attendant is unaware of the contamination and introduces the item onto the sterile field, the entire field has been contaminated.

An additional problem associated with sterile packaging typified by the Banks patent, and by the invention disclosed in my co-pending application, is encountered when items are flash sterilized and immediately delivered from the sterilizer into the sterile field. In this instance, any sterilization wrap, whether woven or non-woven, is undesirable due to the presence of moisture which provides a strike through path for contaminants due to the porosity of the wrap material.

Accordingly, there is a need for a package for receiving a sterilizable item that allows the item to be introduced into a sterile field by a non-sterile attendant without contaminating the sterile field and that eliminates the strike through path for contaminants in a sterile package that has been flash sterilized.

It is therefore an object of the present invention to provide a packaging system, and associated method, for packaging a sterile item for sterile introduction of the item into a sterile field.

A further object of the present invention is to provide a reinforced package that protects the item, and the sterile field into which it will be introduced, from inadvertent contamination.

Still another object of the present invention is to provide a reinforced package that can be flash sterilized without providing a strike through path for contaminants.

Other objects and advantages over the prior art will become apparent to those skilled in the art upon reading the detailed description together with the drawings as described as follows.

BRIEF SUMMARY OF THE INVENTION

In accordance with the teachings of the present invention a package for a sterilizable item is provided. The package includes a tubular member having an open end and a closed end. A reinforcing panel encompassing the closed end is secured to the tubular member proximate the closed end such that the reinforcing panel includes an open end. A cuff portion is attached to the tubular member proximate the open end of the tubular member. The cuff portion includes a first edge secured to the tubular member and a second edge in spaced relation from the first edge, wherein in the cuff portion extends from the open end of the tubular member and substantially overlaps the open end of said reinforcing panel. A portion of the inside surface of the tubular member is thus exposed and defines the width of the cuff portion. In the preferred embodiment, the cuff portion is integral with the tubular member. In this regard, the cuff portion is preferably formed on the tubular member by folding over a circumferential cuff so that a first portion of an outside surface of the tubular member contacts a first portion of the outside surface of the reinforcement panel. A portion of the inside surface of the tubular member is thus exposed and defines the width of the cuff portion.

In addition, an autoclavable moisture barrier is bonded to the reinforcement panel. In this regard, the moisture barrier begins at the closed end along and extends along a portion of the reinforcement panel. The moisture barrier provides a non-porous layer that eliminates a moisture path through the material after the package has been flash sterilized. The reinforcement panel provides a buffer layer between an attendant's grasping hand (not shown) and an item placed within the tubular member such that the attendant's hand is not in direct contact with the layer of material of the tubular member that is in contact with the item. In this manner, an item that has been flash sterilized in the package of the present invention can be delivered into a sterile field, by a non-sterile attendant, without creating a risk

BRIEF DESCRIPTION OF THE SEVERAL VIEWS OF THE DRAWINGS

The above-mentioned features of the invention will become more clearly understood from the following detailed description of the invention read together with the drawings in which:

FIGS. 4a–4d illustrate the steps of folding the package in accordance with the method of the present invention.

DETAILED DESCRIPTION OF THE INVENTION

Figure 1:
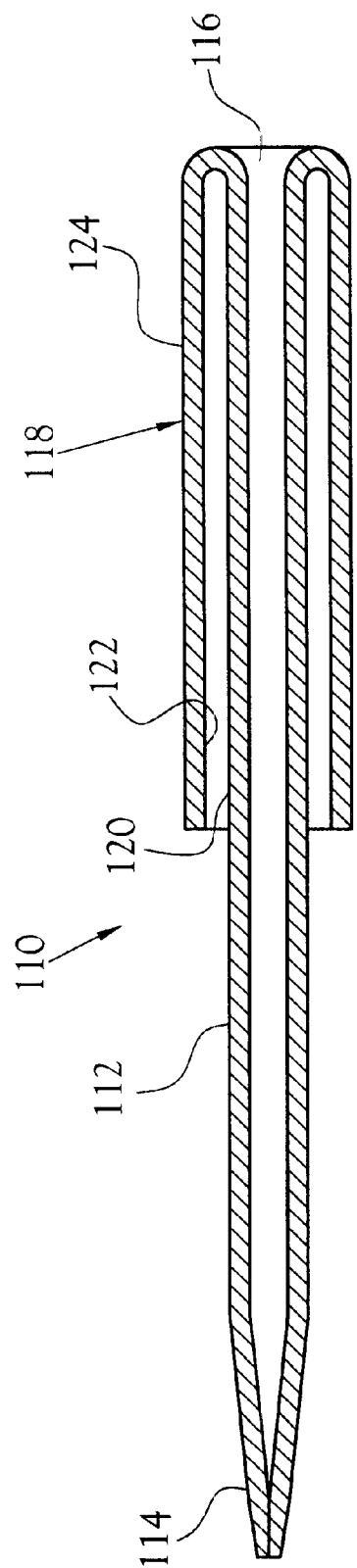
FIG. 1 is a cross-sectional view of a prior art package for a sterilizable item. For purposes of clarity, the illustration is not drawn to scale.
Figure 2:
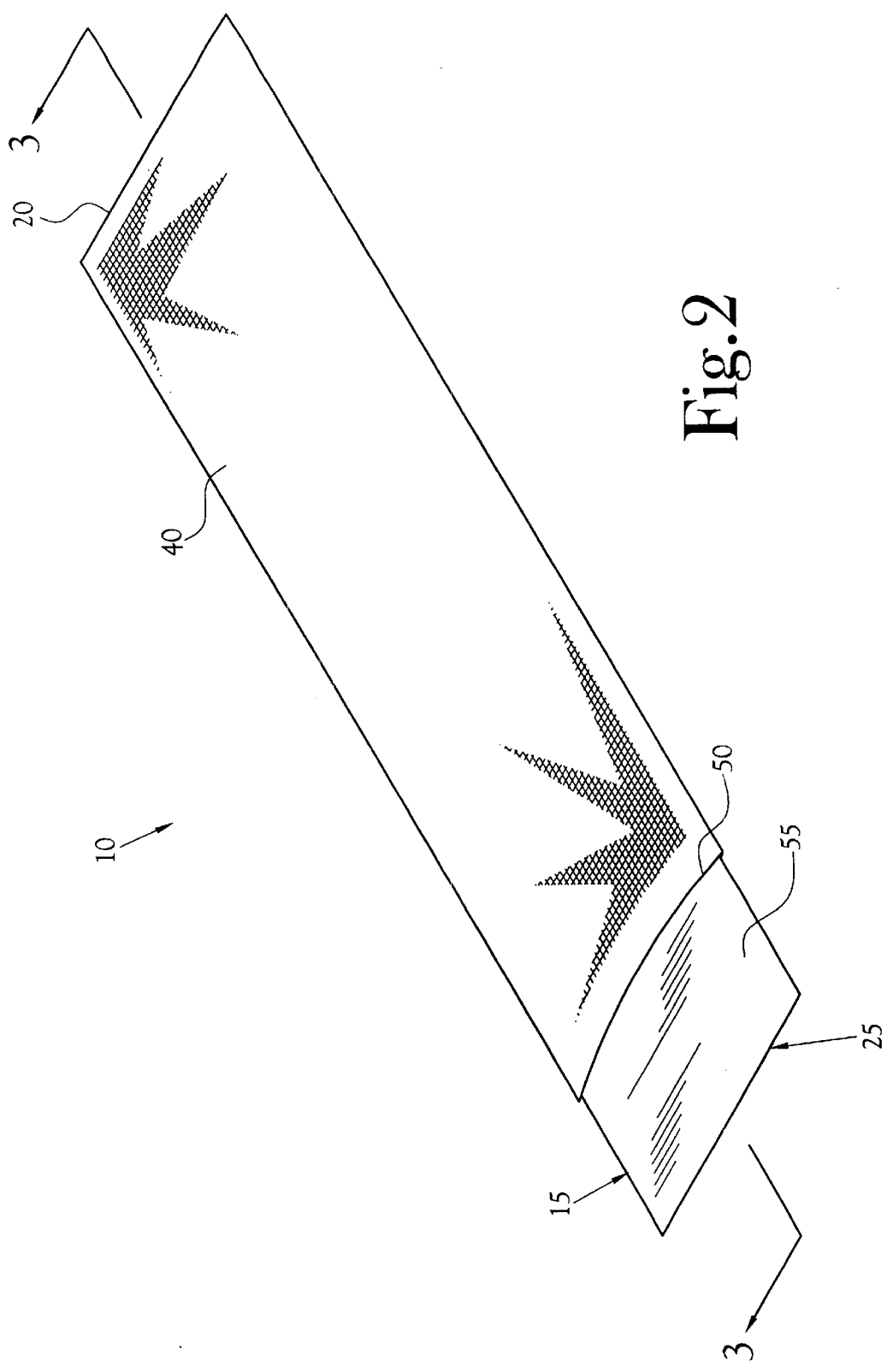
FIG. 2 is a perspective view of the package of the present invention.
Figure 3:
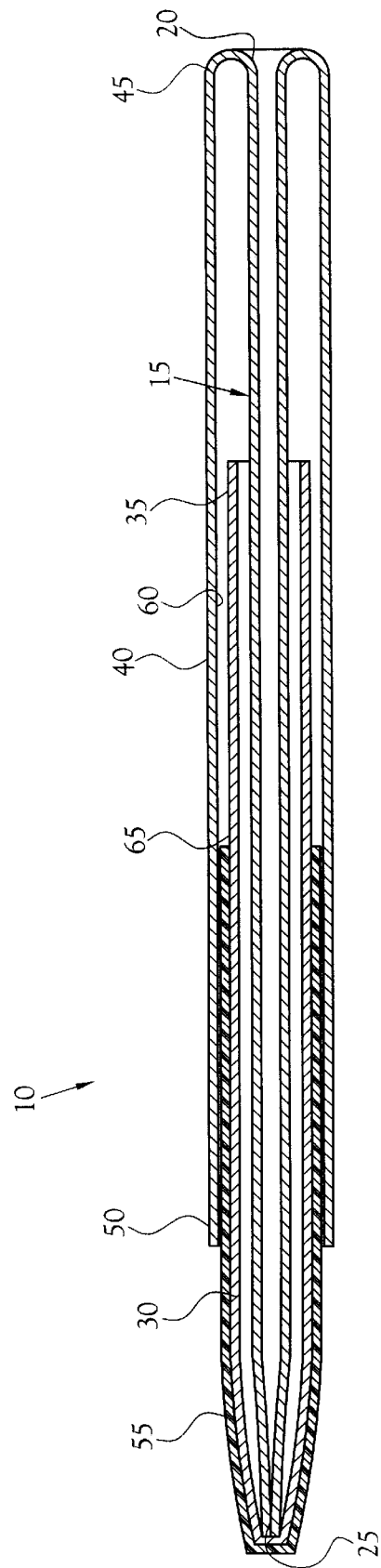
FIG. 3 is a cross-sectional view of the package of the present invention taken along lines 3—3 in FIG. 2. For purposes of clarity, the illustration is not drawn to scale.

A package for a sterilizable item, constructed in accordance with the present invention, is illustrated generally as 10 in the figures. The prior art package 110, illustrated in FIG. 1, includes a flexible tubular member 112 having a closed end 114 and an open end 116 and a border portion 118 that is preferably formed on the tubular member 112 by folding over a circumferential cuff so that a first portion 120 of an outside surface of the tubular member 112 contacts a second portion 122 of the outside surface. A portion 124 of the inside surface of the tubular member 112 is thus exposed and defines the width of the cuff portion. It will be appreciated that the portion of the tubular member 112 proximate the closed end 114 is single ply and thus presents a risk of contaminating the sterilized item (not shown) received within the tubular member 112 if the integrity of the material defining the tubular member 112 is compromised.

In order to overcome this risk, in accordance with the teachings of the present invention, the package 10, seen in FIGS. 2, 3, and 4a–4d includes a tubular member 15 having an open end 20 and a closed end 25. A reinforcing panel 30 encompassing the closed end is secured to the tubular member 15 proximate the closed end 25 such that the reinforcing panel 30 includes an open end 35. A cuff portion 40 is attached to the tubular member 15 proximate the open end 20 of the tubular member 15. The cuff portion 40 includes a first edge 45 secured to the tubular member 15 and a second edge 50 in spaced relation from the first edge 45, wherein in the cuff portion 40 extends from the open end 20 of the tubular member 15 and substantially overlaps the open end 35 of said reinforcing panel 30. A portion of the inside surface of the tubular member 15 is thus exposed and defines the width of the cuff portion 40. In the preferred embodiment, the cuff portion 40 is integral with the tubular member 15. In this regard, the cuff portion 40 is preferably formed on the tubular member 15 by folding over a circumferential cuff so that a first portion 60 of an outside surface of the tubular member 15 contacts a first portion 65 of the outside surface of the reinforcement panel 30. A portion of the inside surface of the tubular member 15 is thus exposed and defines the width of the cuff portion 40.

The item 70 is placed into the tubular member 15 so that the item 70 contacts a portion of an inside surface at the closed end 25 of the tubular member 15. The tubular member 15 is sized in proportion to the particular item 70 to be enclosed by the tubular member 15. The reinforcement panel 30 provides a buffer layer between an attendant's grasping hand (not shown) and the item 70 such that the attendant's hand is not in direct contact with the layer of material of the tubular member 15 that is in contact with the item 70.

Those skilled in the art recognize that under normal steam sterilization a package goes through a drying cycle, which removes the moisture and returns the material to an ambient or lower than ambient moisture condition. At ambient or lower than ambient moisture conditions, state of the art woven or non-woven sterile pack materials are considered to be a suitable barrier to contamination. However, when a pack is flash sterilized, the pack does not go through the drying cycle. And, while all state of the art CSR wrap materials provide moisture protection up to an applied pressure of less than 1 psi, the pressure exerted by the fingers and thumb of an attendant far exceeds 1 psi. The moisture then provides a strike through path for contaminants on the exterior of the pack or on the hands of the attendant to pass through and contaminate the contents of the package. In order to prevent such contamination, a moisture barrier 55 is provided for substantially encasing the closed end 25. In this regard, in the preferred embodiment, moisture barrier 55 is laminated to reinforcement panel 30 and begins a the closed end 25 and extends along a portion of the length of reinforcement panel 30 so as to encase the width, or circumference, of the reinforcement panel 30. Moisture barrier 55 is comprised of an autoclave compatible, non-porous material, such as a heat-resistant plastic film. The material is selected so as to be impervious to moisture in any state, liquid or steam. By only covering a portion of the reinforcement panel 30, the majority of the package 10 is uncovered so as to allow easy and rapid penetration of steam during the flash sterilization process. The moisture barrier 55 provides a moisture impenetrable area to be grasped by an attendant, thus eliminating contamination via a moisture created strike through path. While a preferred embodiment in which the moisture barrier 55 is laminated to the outer surface of the reinforcement panel 30 has been described, those skilled in the art will recognize that the moisture barrier could be laminated to either surface of either of the layers of the package 10 so long as the moisture barrier 55 is interposed between a graspable area of the package 10 and the item to be flash sterilized within the package 10.

In order to secure the item 70 in the tubular member 15, the tubular member is folded in accordance with the preferred folding method described herein. Referring to FIGS. 4a–4b, at least one angular fold line 80 is formed in the cuff portion 40 by folding a corner 75 of the tubular member 15 proximate the open end 20 towards an opposing side 85 of the tubular member 15, thereby forming a point proximate said first edge 45 of the cuff portion thereby substantially closing the upper end 20 of the tubular member 15. In the preferred embodiment, a pair of angular fold lines 80, substantially perpendicular to each other are formed by folding the corners of the tubular member towards each other thereby forming a point 88. A substantially horizontal fold line is formed above the item 70 as the cuff portion 40 is folded over on its self such that point 88 overlaps the second edge 50 as seen in FIG. 4b and 4c. In order to secure the fold, at least a portion of the point 88 is folded under the second edge 50 of the cuff portion 40 as seen in FIG. 4d. Tape (not shown) may be applied to the first side, if desired, to tape the cuff portion to the tubular member to form a tamper-proof seal. The item in the sealed tubular member may also be sterilized without additional packaging. The package 10 system is sterilized by any convenient method suitable for the item and the materials used in the package 10. The package 10 is easily opened for aseptic presentation of the sterile item. The non-scrubbed attendant holds the package 10 in one hand at the closed end of the tubular member 15, with folded under point facing the attendant. With a second hand, the attendant releases the point 88 from being folded under the second edge 50 and unfolds the cuff portion 40. The attendant pulls on the second edge 50 of the cuff portion 40 until the tubular member has been inverted to expose generally the entire inside surface of the tubular member, while in the process covering the attendant's hand and forearm with the inverted tubular member. With hand and forearm thus covered and protected, the non-scrubbed attendant may aseptically place the item 70 directly onto the sterile surgical field, eliminating the need for a scrubbed assistant. More importantly, inasmuch as the reinforcing panel defines an additional layer between the non-scrubbed attendant's hand and the sterile item, the possibility of inadvertent contamination of the item and the sterile field is eliminated.

From the foregoing description, it will be recognized by those skilled in the art that a package for receiving a sterilizable item and that allows the item to be introduced into a sterile field by a non-sterile attendant without contaminating the sterile field offering advantages over the prior art has been provided. Specifically, the package provides a packaging system, and associated method, for packaging a sterile item for sterile introduction of the item into a sterile field and that is reinforced in order to protect the item, and the sterile field into which it will be introduced, from inadvertent contamination.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention, we claim:

1. A package for receiving a sterilizable item, said package comprising:
   a tubular member having an open end and a closed end;
   a reinforcing panel encompassing said closed end and secured to said tubular member proximate said closed end, wherein said reinforcing panel includes an open end;
   a moisture barrier for substantially encasing said closed end of said tubular member, wherein said moisture barrier is constructed of a non-porous, autoclave compatible material; and
   a cuff portion attached to said tubular member proximate said open end, said cuff portion including a first edge secured to said tubular member and a second edge in spaced relation from said first edge, wherein in said cuff portion extends from said open end of said tubular member and substantially overlaps said open end of said reinforcing panel.

2. The package of claim 1 wherein said cuff portion and said tubular member are integral.

3. The package of claim 1 wherein said package is constructed of a sterilizable material.

4. The package of claim 1 wherein said autoclave compatible material is plastic.

5. A method for packaging a sterilizable item for aseptic presentation, comprising:
   (a) placing the item into a sterilizable tubular member so that the item contacts a portion of an inside surface at a closed end of said tubular member, wherein said tubular member includes a reinforcing panel encompassing said closed end and secured to said tubular member proximate said closed end, wherein said reinforcing panel includes an open end, and said tubular member further includes a moisture barrier for substantially encasing said closed end of said tubular member, wherein said moisture barrier is constructed of a non-porous, autoclave compatible material;
   (b) forming a cuff portion on said tubular member, a first edge of said cuff portion being attached to said tubular member proximate an opening in said tubular member for the circumference of said opening and a second opposing edge of said cuff portion being spaced apart from said first edge by a width of said cuff portion;
   (c) forming at least one angular fold line in said cuff thereby forming a point proximate said first edge of said cuff portion whereby said open end is substantially closed;
   (d) forming a fold line in said cuff portion and said tubular member above said item and below said point whereby said point overlaps said second edge of said cuff; and (e) thereafter placing at least a portion of said point under said second edge of said cuff portion.

6. The method of claim 5 wherein in step (d) at least a portion of said inside surface of a first side of said tubular member is in contact with at least a portion of said inside surface of a second side of said tubular member.

7. The method of claim 5 wherein said cuff portion is formed by folding over a circumferential portion of said tubular member so that a first portion of an outside surface of said tubular member is in contact with a second portion of said reinforcing panel, and a portion of an inside surface of said tubular member defines said width of said cuff portion.

8. The method of claim 7 wherein a pair of angular fold lines are formed such that said point is proximate a longitudinal center line of said outside surface of said tubular member.

9. The method of claim 5 wherein said second edge of said cuff portion is located proximate the middle third of the item in said tubular member.

10. The method of claim 5 including the step of sterilizing said packaged item.

11. A package for receiving a sterilizable item, said package comprising:
- a tubular member having an open end and a closed end, wherein said tubular member is constructed of a sterilizable material;
- a cuff portion attached to and integral with said tubular member proximate said open end, said cuff portion including a first edge secured to said tubular member and a second edge in spaced relation from said first edge, wherein in said cuff portion extends from said open end of said tubular member and substantially overlaps said open end of said reinforcing panel;
- a reinforcing panel encompassing said closed end and secured to said tubular member proximate said closed end, wherein said reinforcing panel includes an open end; and
- a moisture barrier for substantially encasing said closed end of said tubular member, wherein said moisture barrier is constructed of a non-porous, autoclave compatible material.

* * * * *